(12) United States Patent
Miller

(10) Patent No.: US 7,838,272 B2
(45) Date of Patent: Nov. 23, 2010

(54) INCREASED YIELD IN GAS-TO-LIQUIDS PROCESSING VIA CONVERSION OF CARBON DIOXIDE TO DIESEL VIA MICROALGAE

(75) Inventor: Stephen Joseph Miller, San Francisco, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 631 days.

(21) Appl. No.: 11/782,960

(22) Filed: Jul. 25, 2007

(65) Prior Publication Data

US 2009/0029427 A1 Jan. 29, 2009

(51) Int. Cl.
*C12P 5/02* (2006.01)
*C10L 1/04* (2006.01)
*C10L 1/16* (2006.01)

(52) U.S. Cl. .......................... 435/167; 208/15; 208/27; 208/97; 585/1; 585/14; 585/240; 585/739; 585/740; 585/750; 585/751; 435/134; 435/166; 435/289.1; 435/303.1

(58) Field of Classification Search ................ None
See application file for complete search history.

(56) References Cited

U.S. PATENT DOCUMENTS

| | | | |
|---|---|---|---|
| 4,859,312 A | 8/1989 | Miller | |
| 4,992,605 A | 2/1991 | Craig et al. | |
| 5,158,665 A | 10/1992 | Miller | |
| 5,300,210 A | 4/1994 | Zones et al. | |
| 6,204,426 B1 | 3/2001 | Miller et al. | |
| 6,630,066 B2 | 10/2003 | Cash et al. | |
| 6,723,889 B2 | 4/2004 | Miller et al. | |
| 6,841,063 B2 | 1/2005 | Elomari | |
| 6,846,402 B2 | 1/2005 | Hemighaus et al. | |
| 7,501,546 B2 * | 3/2009 | Koivusalmi et al. | ......... 585/327 |
| 2003/0203983 A1 | 10/2003 | O'Rear et al. | |
| 2007/0048859 A1 | 3/2007 | Sears | |
| 2007/0131579 A1 | 6/2007 | Koivusalmi et al. | |

FOREIGN PATENT DOCUMENTS

| | | |
|---|---|---|
| WO | WO 9711154 | 3/1997 |
| WO | WO 03024604 | 3/2003 |
| WO | WO 2005013671 | 2/2005 |
| WO | WO 2007070452 | 6/2007 |
| WO | WO 2008040980 | 4/2008 |

OTHER PUBLICATIONS

Antolín et al., "Optimisation of Biodiesel Production by Sunflower Oil Transesterification," Bioresource Technology, vol. 83, pp. 111-114 (2002).
Baum, R., "Microalgae are Possible Source of Biodiesel Fuel," Chem. & Eng. News, vol. 72(14), pp. 28-29 (1994) [Abstract].
Huber et al., "Synthesis of Transportation Fuels from Biomass: Chemistry, Catalysts, and Engineering," Chem. Rev., vol. 106, pp. 4044-4098 (2006).
Ragauskas et al., "The Path Forward for Biofuels and Biomaterials," Science, vol. 311, pp. 484-489 (2006).
Rana et al., "A Review of Recent Advances on Process Technologies for Upgrading of Heavy Oils and Residua," Fuel, vol. 86, pp. 1216-1231 (2007).
Sousa-Aguiar at al., "Natural Gas Transformations: The Path to Refining in the Future," Catalysis Today, vol. 101, pp. 3-7 (2005).

* cited by examiner

*Primary Examiner*—Herbert J. Lilling
(74) *Attorney, Agent, or Firm*—Edward T. Mickelson

(57) ABSTRACT

The present invention is generally directed to systems and methods for integrating gas-to-liquids (GTL) processing with biofuels production. In some embodiments of the present invention, carbon dioxide ($CO_2$) generated by GTL processing is used to support grovel (via photosynthesis) of microalgae. In some such embodiments, the microalgae can be further processed to yield a diesel fuel that can be used either by itself, or mixed with fuel produced by the GTL processing.

35 Claims, 5 Drawing Sheets

INCREASED YIELD IN GAS-TO-LIQUIDS PROCESSING VIA CONVERSION OF CARBON DIOXIDE TO DIESEL VIA MICROALGAE

FIELD OF THE INVENTION

This invention relates generally to an integration of gas-to-liquids (GTL) processing with biofuels production, and specifically to methods and systems for utilizing carbon dioxide ($CO_2$) produced during GTL processing to support photosynthesis in microalgae—a biofuels precursor.

BACKGROUND

1. Carbon Dioxide Emissions

Carbon dioxide ($CO_2$) is a well-known greenhouse gas and attempts to reduce the emissions of this gas into the atmosphere are desirable. $CO_2$ is commonly formed when hydrocarbon-based materials are processed. As an example, a gas-to-liquids (GTL) process converts roughly two-thirds of the starting gas (methane or natural gas) into hydrocarbon-based liquid products, with the other one-third being emitted as $CO_2$. See, e.g., Sousa-Aguiar et al., "Natural Gas Transformations: The Path to Refining in the Future," Catalysis Today, vol. 101, pp. 3-7, 2005. The current high costs associated with capturing and/or utilizing this $CO_2$ using conventional amine scrubbing technology coupled with sequestration of high pressure $CO_2$ are such that doing so is generally not economically-viable.

2. Biofuels

A common route to making transportation fuels is to convert vegetable oils to biodiesel via transesterification of the triglyceride species contained therein, so as to yield fatty acid methyl esters. See, e.g., Huber et al., "Synthesis of Transportation Fuels from Biomass: Chemistry, Catalysts, and Engineering," Chem. Rev., vol. 106, pp. 4044-4098, 2006; and Antolín et al., "Optimisation of Biodiesel Production by Sunflower Oil Transesterification," Bioresource Technology, vol. 83, pp. 111-114, 2002. However, a major drawback of this type of biodiesel is that the fatty acid methyl esters (FAME) generally have poor oxidation stability and poor low temperature performance (i.e., high cloud and pour points). One way around this is to hydroprocess the vegetable oil to separate the fatty acid-derived paraffins from the species comprising oxygen-containing functional groups, and to then isomerize the isolated paraffins via an isomerization process (see, e.g., Zones et al., U.S. Pat. No. 5,300,210) to produce a low pour point diesel. Such a process, however, still has the drawback that production is limited by the supply of vegetable oil—which in many cases leads to a competition of fuel versus food. See Ragauskas et al., "The Path Forward for Biofuels and Biomaterials," Science, vol. 311, pp. 484-489, 2006.

Reducing $CO_2$ emissions via routes other than sequestration are also challenging. The exceptional thermodynamic stability of this molecule makes its chemical conversion likewise quite costly. Accordingly, a cost-effective way (method) of mitigating $CO_2$ emissions in GTL processing would be a welcome development, particularly wherein such a method could be further used to support the production of high-quality biofuels with a feedstock that does not compete directly with food.

BRIEF DESCRIPTION OF THE INVENTION

The present invention is generally directed to systems and methods for integrating gas-to-liquids (GTL) processing with biofuels production. In some embodiments of the present invention, carbon dioxide ($CO_2$) generated by GTL processing is used to support growth (via photosynthesis) of microalgae. In some such embodiments, the microalgae can be further processed to yield a diesel and/or other fuel that can be used either by itself, or mixed with fuel produced by the GTL processing.

In some embodiments, the present invention is directed to a method comprising: the steps of (1) generating $CO_2$ in a gas-to-liquids plant; (2) using at least some of the $CO_2$ generated in the gas-to-liquids plant to grow microalgae by supporting photosynthesis in their growth cycle, wherein such growth yields harvestable microalgae; (3) harvesting the microalgae and processing the harvested microalgae to yield a triglyceride-based biofuel precursor; (4) hydroprocessing the triglyceride-based biofuel precursor to yield paraffins; and (5) optionally isomerizing the paraffins to yield a transportation fuel.

In some embodiments, the present invention is directed to a system comprising: (1) a conventional gas-to-liquids plant that produces a $CO_2$ by-product; (2) a repeatedly-harvestable population of microalgae; (3) a means for directing the $CO_2$ to the microalgae to support growth thereof; (4) a means for harvesting the microalgae and extracting from it a triglyceride-based product; (5) a means for hydroprocessing at least a portion of the triglyceride-based product to yield a paraffin-based product; and (6) an optional means for isomerizing at least a portion of the paraffin-based product to yield a transportation fuel.

In some embodiments, a key aspect of the present invention is the above-mentioned integration of biofuels processing with traditional gas-to-liquids processing. Such integration can be found in both the above-described methods and systems, and it can be tailored to yield a number of advantages in a variety of processing schemes and/or systems. Such advantages will be further described in the Examples provided herein.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

1. Introduction

Figure 1:
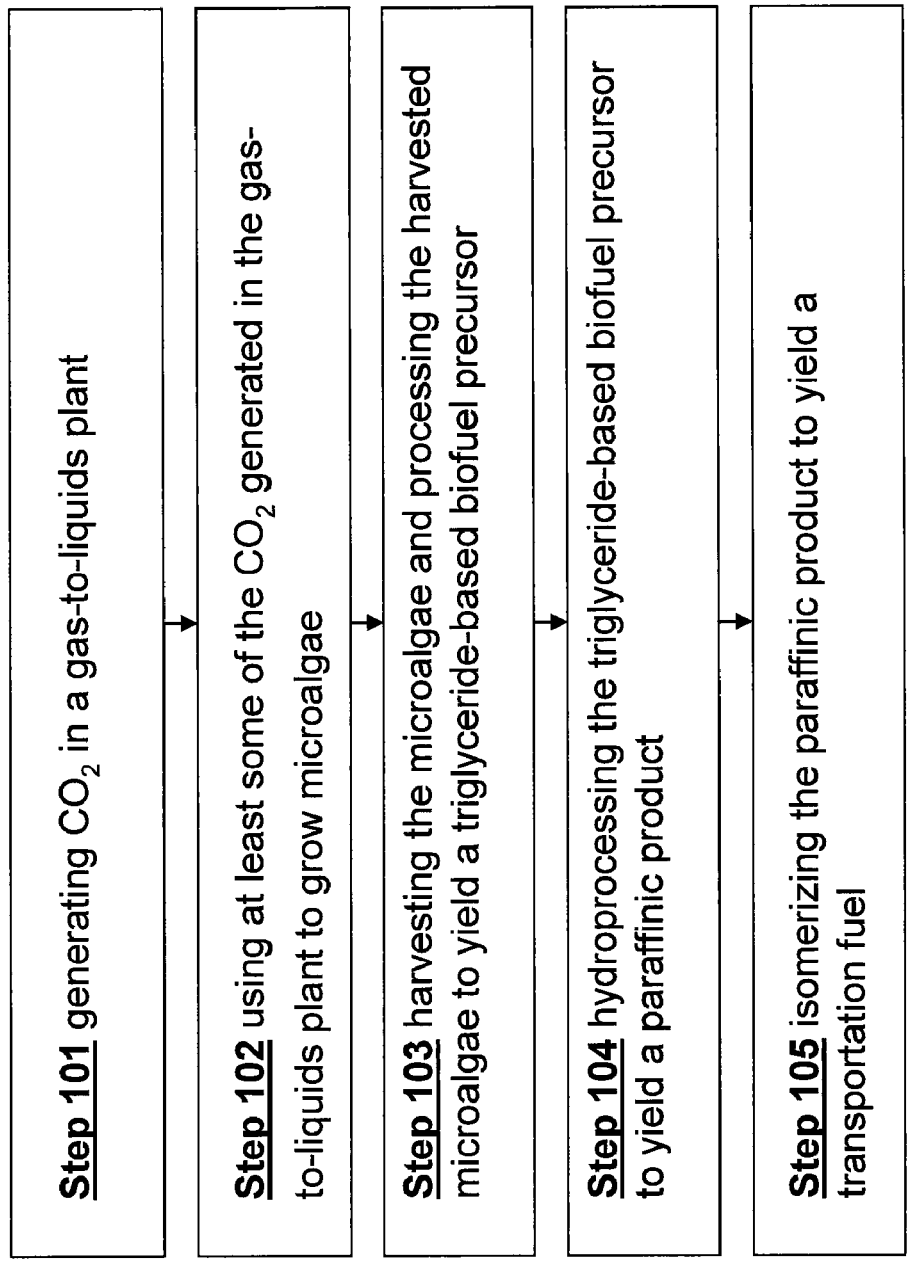
FIG. 1 depicts, in stepwise fashion, a method for directing gas-to-liquids (GTL) processing-derived $CO_2$ to microalgae to support their photosynthetically-driven growth, and to harvesting and processing this microalgae to generate biofuels, in accordance with some embodiments of the present invention.

A potentially-important way to make vegetable oil-like triglycerides that do not compete with food (see above), and that could be produced in much higher volume, is to use new, highly-productive strains of microalgae. These microalgae are known to give as much as 150 times the yield of triglycerides per acre than soybeans. They also afford tremendous flexibility in that they can grow in arid locations or off-shore, and they can grow in saline water. They are typically grown in very shallow pools (e.g., a few inches deep) over a large area (e.g., a few acres). For high yields, however, they typically require the supplemental addition of large amounts of $CO_2$. See R. Baum, "Microalgae are Possible Source of Biodiesel Fuel," Chem. & Eng. News, vol. 72(14), pp. 28-29, 1994.

As mentioned in an earlier section, the present invention is generally directed to systems and methods for integrating gas-to-liquids (GTL) processing with biofuels production. In an effort to reduce carbon dioxide ($CO_2$) emissions and to utilize biofuel precursors that do not compete with food, in some embodiments of the present invention, $CO_2$ generated by GTL processing is used to support growth (via photosynthesis) of microalgae. In some such embodiments, the microalgae can be further processed to yield a transportation fuel (e.g., diesel) that can be used either by itself, or mixed with fuel produced by the GTL or other processing. In some embodiments, processing of the microalgae (or products derived therefrom) can be at least partly integrated with the GTL processing.

2. Definitions

Certain terms and phrases are defined throughout this description as they are first used, while certain other terms used in this description are defined below:

"Gas-to-liquids" ("GTL"), as defined herein, refers to processes that convert gaseous hydrocarbons, such as natural gas, to higher molecular weight (i.e., "liquid" and/or "waxy") hydrocarbons. Typically, such processes proceed through a syngas (vide infra) intermediate which is then converted to alkanes (paraffins) via a catalytic Fischer-Tropsch process.

"Synthesis gas" or "syngas" is a gaseous mixture containing carbon monoxide and hydrogen and optionally other gases such as water and carbon dioxide. Syngas is typically produced by steam reforming of carbon- or hydrocarbon-containing precursors.

Steam reforming of coal yields syngas according to the following equation:

$$C + H_2O \rightarrow H_2 + CO$$

Steam reforming of natural gas yields syngas according to the following reaction:

$$CH_4 + H_2O \rightarrow CO + 3H_2$$

General oxidative routes from hydrocarbons to syngas are as follows:

$$C_nH_{(2n+2)} + (n/2)O_2 \rightarrow nCO + (n+1)H_2$$

As mentioned above, syngas can be catalytically-converted to paraffins (alkanes) via a catalytic Fischer-Tropsch (FT) process:

$$nCO + (2n+1)H_2 \rightarrow C_nH_{(2n+2)} + nH_2O$$

where typical catalysts include iron and cobalt. Examples of the Fisher-Tropsch process are described in U.S. Pat. No. 6,846,402.

In addition to the reactions shown above, it is worth noting that CO from syngas can undergo a "water-gas shift (WGS)" reaction to produce $CO_2$ and $H_2$:

$$CO + H_2O \rightarrow CO_2 + H_2$$

"Microalgae," as defined herein, refers generally to species of photosynthetically-responsive microbes. Species or strains of such microalgae used in embodiments of the present invention can be chosen based on factors such as growth rate, triglyceride type and yield, processability, and the like.

"Triglyceride," as defined herein, refer to class of molecules having the following molecular structure:

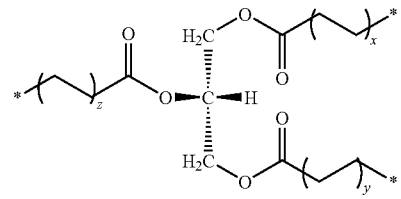

where x, y, and z can be the same or different, and wherein one or more of the branches defined by x, y, and z can have unsaturated regions. For the production of diesel fuels, it is often desirable that at least one of x, y, and/or z be equal to 4 to 10, such that, upon hydroprocessing, they yield paraffins in the C8 to C21 range (vide infra).

"Triglyceride-based," as defined herein, refers to biofuel precursor material comprising triglyceride species in the majority (by weight), but possibly also comprising other oxygenate species such as free fatty acids.

"Hydroprocessing" refers to processes that react a hydrocarbon-based material with hydrogen, typically under pressure and with a catalyst (hydroprocessing can be non-catalytic). Such processes include, but are not limited to, hydrodeoxygenation (of oxygenated species), hydrotreating, hydrocracking, hydroisomerization, and hydrodewaxing. For examples of such processes, see Cash et al., U.S. Pat. No. 6,630,066; and Elomari, U.S. Pat. No. 6,841,063. Embodiments of the present invention utilize such hydroprocessing to convert triglycerides to paraffins.

While "hydrocarbons" are substantially comprised of carbon and hydrogen, hydrocarbon-based materials can include molecules with heteroatoms, e.g., alcohols, carboxylic acids, and the like; the heteroatoms generally being atoms other than C or H, and typically atoms selected from the group consisting of O, N, S, P, and combinations thereof.

"Isomerizing," as defined herein, refers to catalytic processes that typically convert n-alkanes to branched isomers. ISODEWAXING (Trademark of CHEVRON U.S.A. INC.) catalysts are representative catalysts used in such processes. See, e.g., Zones et al., U.S. Pat. No. 5,300,210; Miller, U.S. Pat. No. 5,158,665; and Miller, U.S. Pat. No. 4,859,312.

"Transportation fuels," as defined herein, refer to hydrocarbon-based fuels suitable for consumption by vehicles. Such fuels include, but are not limited to, diesel, gasoline, jet fuel and the like.

3. Methods

As mentioned previously, and with reference to FIG. 1, in some embodiments the present invention is directed to methods comprising the steps of: (Step 101) generating $CO_2$ in a gas-to-liquids (GTL) plant; (Step 102) using at least some of the $CO_2$ generated in the gas-to-liquids plant to grow microalgae by supporting photosynthesis in their growth cycle, wherein such growth yields harvestable microalgae; (Step 103) harvesting the microalgae and processing the harvested microalgae to yield a triglyceride-based biofuel precursor; (Step 104) hydroprocessing the triglyceride-based biofuel precursor to yield a paraffinic product; and (Step 105) optionally isomerizing the paraffinic product to yield a transportation fuel (note that, depending on the product desired, Step 105 may not be necessary). Typically, such a gas-to-liquids plant is operable for producing transportation fuels.

In some such above-described method embodiments, the use of at least some of the $CO_2$ generated in the gas-to-liquids plant to grow microalgae involves dissolving said $CO_2$ in an aqueous solution. In some such embodiments, the aqueous solution comprises caustic (pH>7) and/or saline water. In some or other such embodiments, the microalgae are initially contained within the aqueous solution (prior to the addition of $CO_2$). In other such embodiments, the aqueous solution is delivered to the microalgae before, during, or after addition of $CO_2$. In still other embodiments, the use of at least some of the $CO_2$ generated in the gas-to-liquids plant to grow microalgae involves sequestering said $CO_2$ through the use of gas separation membranes and subsequently delivering the sequestered $CO_2$ to the microalgae.

In some such above-described method embodiments, the step of harvesting comprises removal of at least some of the microalgae for subsequent processing (typically, a quantity sufficient for timely population replenishment is allowed to remain). In some such embodiments, the subsequent processing serves to extract triglycerides from the microalgae. In some such embodiments, the subsequent processing comprises a process technique selected from the group consisting of dewatering, grinding, crushing, sonication, homogenization, solvent extraction, and combinations thereof. In some such above-described method embodiments, the triglyceride-based biofuel precursor comprises at least 75 weight percent triglycerides.

In some such above-described method embodiments, the step of hydroprocessing comprising processing the triglyceride-based biofuel precursor is carried out in a hydrogen-containing environment in the presence of a catalyst. In some embodiments, the triglyceride-based biofuel precursor would be in the form of an oil that could be blended with traditional refinery feed going on to be hydroprocessed. In some or other embodiments, the triglyceride-based precursor can be hydroprocessed separately from the GTL plant. For a general review of hydroprocessing, see, e.g., Rana et al., "A Review of Recent Advances on Process Technologies for Upgrading of Heavy Oils and Residua," Fuel, vol. 86, pp. 1216-1231, 2007. Integration of the biofuel processing with traditional GTL processing will be discussed in more detail below.

Catalysts used in the above-described hydroprocessing include, but are not limited to, commercially-available hydroprocessing catalysts such as cobalt-molybdenum (Co—Mo) catalysts, nickel-molybdenum (Ni—Mo) catalysts, and noble metal catalysts such as Pd. Hydroprocessing conditions generally include temperature in the range 350° C.-450° C. and pressure in the range of about 4.8 MPa to about 15.2 MPa. For an example of how triglycerides can be hydroprocessed to yield a paraffinic product, see Craig et al., U.S. Pat. No. 4,992,605.

In some such above-described method embodiments, the paraffinic product typically comprises at least 75 weight percent paraffinic species, and more typically comprises at least 80 weight percent paraffinic species. In some such embodiments, C5-C20 paraffins (i.e., hydrocarbons containing between 5 and 20 carbon atoms) account for at least 75 weight percent of the paraffinic species.

In some such above-described method embodiments, the step of isomerizing results in superior fuel properties relative to those of the paraffinic product (although the paraffinic product itself could find use as a fuel or other commodity). In some such embodiments, the step of isomerizing is carried out using an isomerization catalyst. Suitable such isomerization catalysts can include, but are not limited to Pt or Pd on a support such as, but further not limited to, SAPO-11, SM-3, SSZ-32, ZSM-23, ZSM-22, and similar such supports. In some or other embodiments, the step of isomerizing the paraffinic product comprises use of a Pt or Pd catalyst supported on an acidic support material selected from the group consisting of beta or zeolite Y molecular sieves, $SiO_2$, $Al_2O_3$, $SiO_2$—$Al_2O_3$, and combinations thereof. In some such embodiments, the isomerization is carried out at a temperature between about 500° F. and about 750° F. The operating pressure is typically 200-2000 psig, and more typically 200-1000 psig. Hydrogen flow rate is typically 500-5000 SCF/barrel. For other suitable isomerization catalysts, see Zones et al., U.S. Pat. No. 5,300,210; Miller, U.S. Pat. No. 5,158,665; and Miller, U.S. Pat. No. 4,859,312. Similar to the hydroprocessing step, the isomerizing step can be fully or partially integrated with the isomerization of GTL-produced paraffins.

With regard to the catalytically-driven isomerizing step described above, in some embodiments, the methods described herein may be conducted by contacting the paraffinic product with a fixed stationary bed of catalyst, with a fixed fluidized bed, or with a transport bed. In one presently contemplated embodiment, a trickle-bed operation is employed, wherein such feed is allowed to trickle through a stationary fixed bed, typically in the presence of hydrogen. For an illustration of the operation of such catalysts, see Miller et al., U.S. Pat. Nos. 6,204,426 and 6,723.889.

In some such above-described method embodiments, there further comprises a step of blending the transportation fuel with other transportation fuels. In some such above-described method embodiments, the transportation fuel is a low pour-point diesel.

4. Systems

Figure 2:
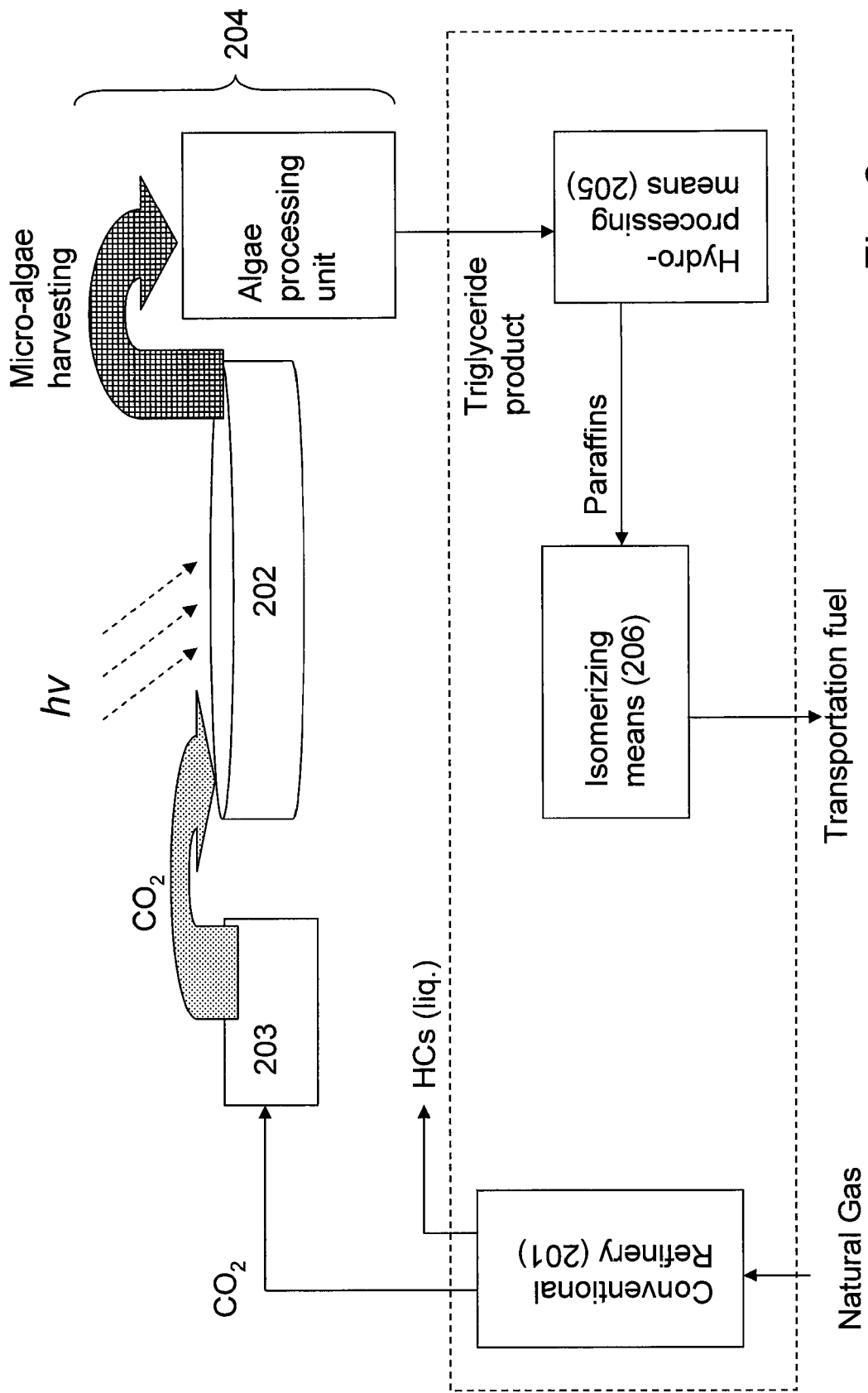
FIG. 2 illustrates, in flow diagram form, a system for generating a commercial biofuel product from GTL processing-derived waste.

As already mentioned in a previous section, and with reference to FIG. 2, in alternate embodiments the present invention is directed to systems comprising: a conventional (i.e., traditional) GTL, plant 201 that produces a $CO_2$ by-product; a repeatedly-harvestable population of microalgae 202; a means 203 for directing the $CO_2$ to the microalgae to support growth thereof; a means 204 for harvesting the microalgae and extracting from it a triglyceride-based product; a means 205 for hydroprocessing at least a portion of the triglyceride-based product to yield a paraffin-based product; and an optional means 206 for isomerizing at least a portion of the paraffin-based product to yield a transportation or other fuel. In some such embodiments, the conventional GTL plant is operable for producing transportation fuels. Note that means 205 and/or means 206 can be integrated or otherwise associated with GTL plant 201, or they can be separate and distinct (hence the dashed box).

In some such above-described system embodiments, the means for directing the $CO_2$ to the microalgae comprises a subsystem means for sequestering the $CO_2$ produced in the GTL plant. In some such embodiments, the subsystem means for sequestering the $CO_2$ produced in the GTL plant involves gas separation. In other such embodiments, the $CO_2$ is sequestered in an aqueous solution. In some such embodiments, the aqueous solution comprises the repeatedly-harvestable population of microalgae. In some or other such embodiments, the aqueous solution is delivered to the repeatedly-harvestable population of microalgae.

In some such above-described system embodiments, the means for harvesting involves removal of at least some of the repeatedly-harvestable population of microalgae for subsequent processing. In some such embodiments, the means for extracting comprises a subsystem means selected from the group consisting of dewatering, grinding, crushing, sonication, homogenization, solvent extraction, and combinations thereof.

In some such above-described system embodiments, the means for hydroprocessing comprises a catalyst and a hydrogen-containing environment, Such hydroprocessing means are not particularly limited, but generally consistent with the methods described above. See, e.g., Craig et al., U.S. Pat. No. 4,992,605. In some embodiments, the triglyceride-based product is co-fed, along with GTL-produced hydrocarbons, into a common hydroprocessing means.

In some such above-described system embodiments, the means for isomerizing comprises an isomerizing (isomerization) catalyst. As in the case of the hydroprocessing, the means for isomerizing are generally consistent with the isomerizing described in the methods above. See, e.g., Zones et al., U.S. Pat. No. 5,300,210. In some or other embodiments, the paraffin-based product is co-fed, along with (CTL-produced hydrocarbons, into a shared means for isomerizing.

In some such above-described system embodiments, the system further comprises a means for blending the transportation fuel with other species to impart to it desirable properties.

5. Integrated Processes and Systems

As already alluded to, a key feature of the present invention is the ease with which biofuels processing can be fully or partially integrated with traditional GTL, processing. Such integration can be seen in both the methods and system embodiments described above. Additionally, the triglyceride product feeds described above can be mixed or blended with other sources of triglycerides (vegetable oils or animal fats) at any suitable process step or system element described above. Exemplary integration schemes are described in Examples 3-5 below.

6. Examples

The following examples are provided to demonstrate particular embodiments of the present invention. It should be appreciated by those of skill in the art that the methods disclosed in the examples which follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

Example 1

This Example serves to illustrate how aspects of the present invention may be implemented, in accordance with some embodiments of the present invention.

Carbon dioxide from a GTL plant is circulated through shallow pools of microalgae to enhance their rate of growth and, correspondingly, the production of triglycerides (see above). In such a case, the microalgae would likely be situated in the vicinity of the GTL plant to ease logistical burdens. It is contemplated that a 3000 BPCD diesel microalgae farm would require about 10 square miles of land, and consume about 2600 tons of $CO_2$ per day. The microalgae is then harvested and the triglycerides (about 60 percent of the total dry weight) recovered. The resulting oil is then blended into the feed going to the hydroprocessing section of the GTL plant for conversion to diesel by either hydrocracking or hydrotreating/ISODEWAXINIG. Overall GTL yield of diesel is thereby increased and the net ($CO_2$ emissions decreased.

Example 2

This Example serves to illustrate a related embodiment for practicing at least some aspects of the present invention wherein the related embodiment involves an offshore platform for producing natural gas.

Carbon dioxide is separated from natural gas (e.g. via membranes or amine treating, with the former typically being the more preferred on an offshore platform due to space and weight considerations) on an offshore platform producing natural gas, then used to feed an algae farm groping around the platform. This can reduce the amount of $CO_2$ that needs to be sequestered onshore. Alternatively, the CO, from such a process can be separated onshore, and used to feed the algae grown onshore and/or offshore.

Example 3

This Example serves to illustrate the integration of biofuels processing with GTL processing, wherein such integration occurs prior to, or during, the hydroprocessing stage.

Figure 3:
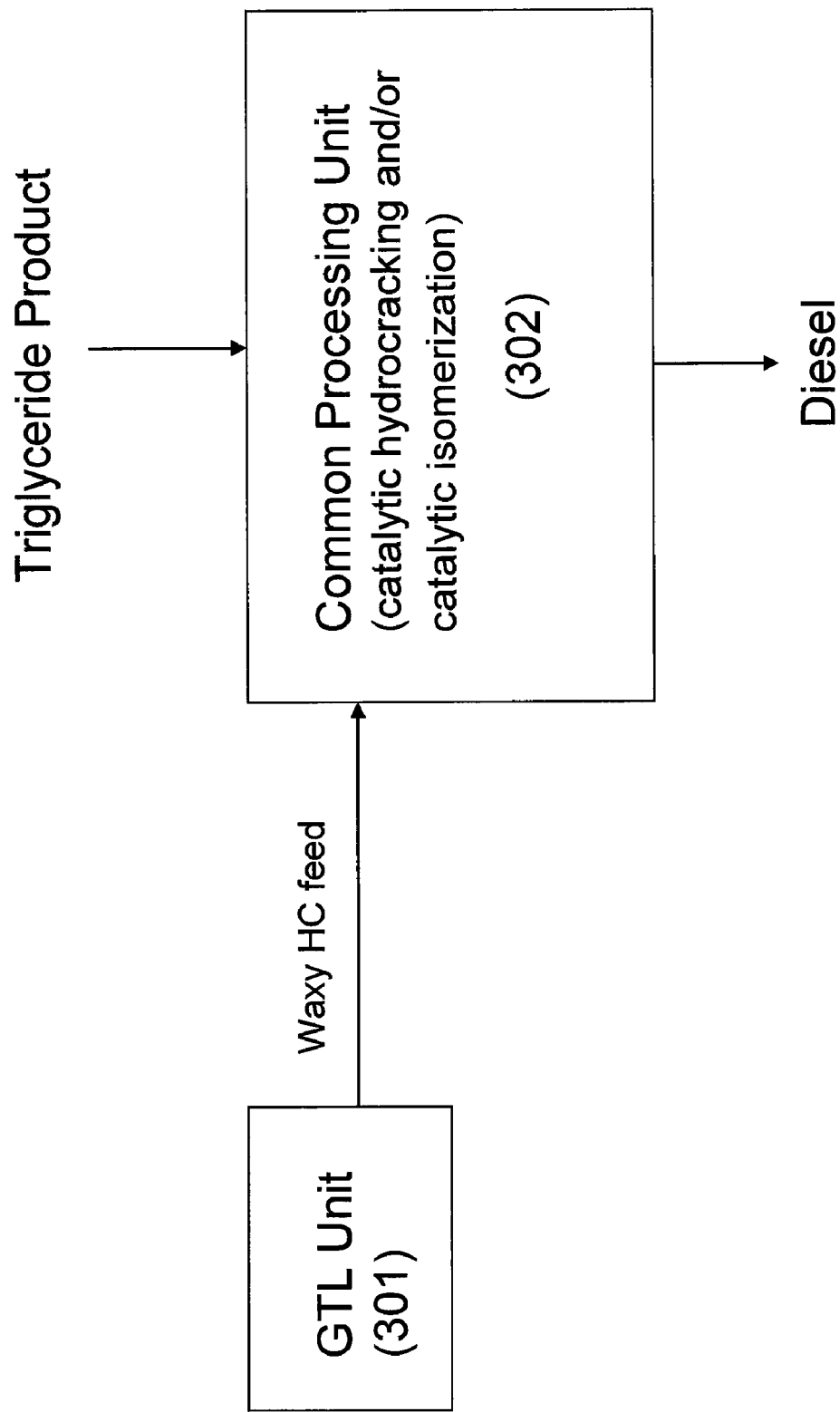
FIG. 3 illustrates, in flow diagram form, the integration of biofuels processing with GTL processing, wherein such integration occurs prior to, or during, the hydroprocessing stage.

Referring to FIG. 3, a waxy hydrocarbon (HC) feed from a GTL processing unit 301 is combined with a bio-derived triglyceride product in a common (or shared) processing unit 302, wherein the common processing unit can provide any of the following: catalytic hydrocracking, catalytic hydrocracking/isomerization, or catalytic isomerization. Such integration can allow for an economy of scale, since hydroprocessing both the syngas-derived paraffins (from the GTL processing) and the triglycerides in the same unlit reduces the cost per barrel of product.

Example 4

This Example serves to illustrate the integration of biofuels processing with GTL processing, wherein such integration occurs after the GTL HCs have been hydrocracked, but before isomerization.

Figure 4:
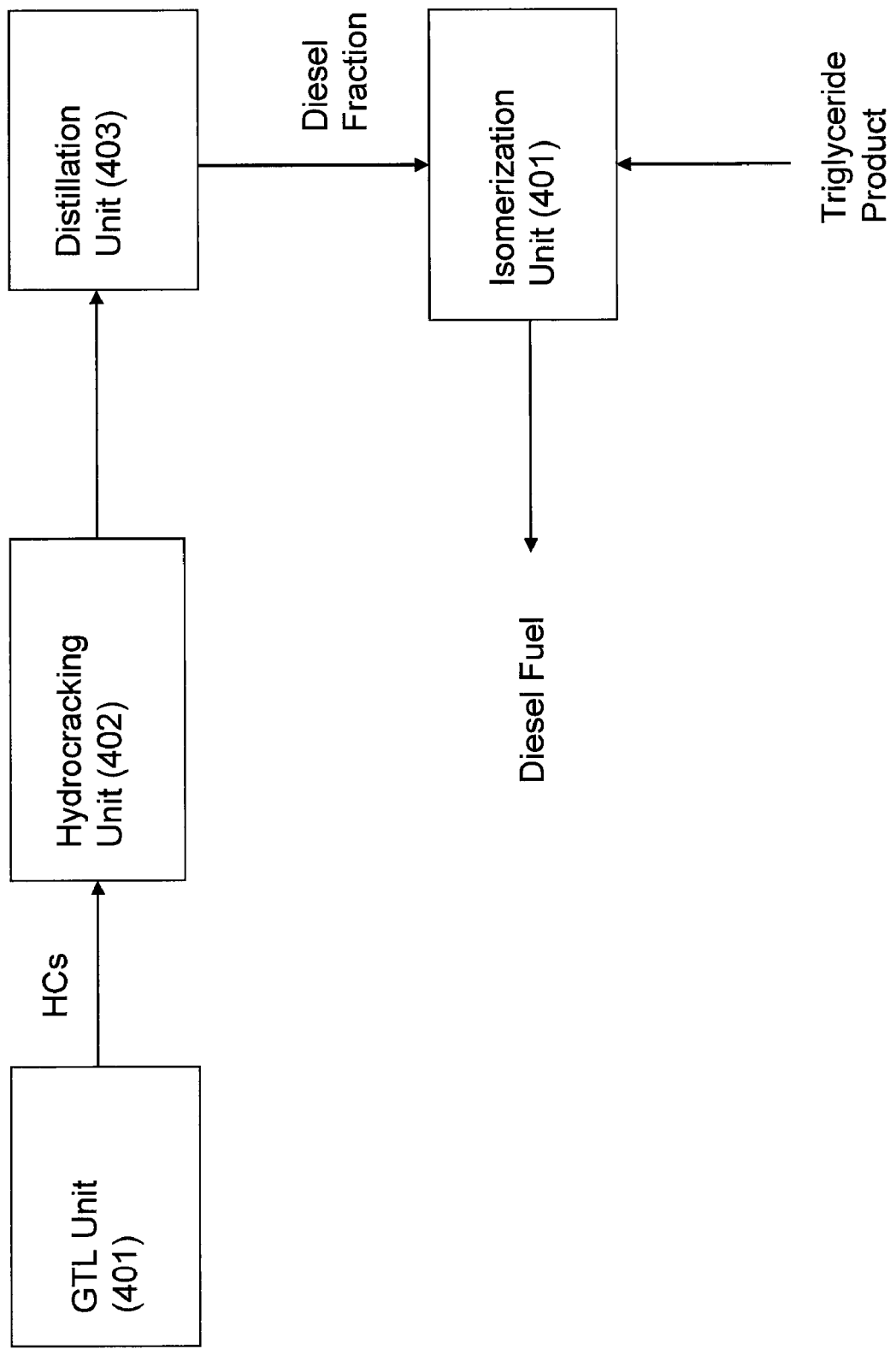
FIG. 4 illustrates, in flow diagram form, the integration of biofuels processing with GTL processing, wherein such integration occurs after the GTL hydrocarbons (HCs) have been hydrocracked, but prior to subjecting them to any isomerization process.

Referring to FIG. 4, hydrocarbons generated by GTL processing unit 401 are hydroprocessed in hydrocracking unit 402, the product of which is distilled in distillation unit 403 and the diesel fraction obtained therefrom is co-fed with triglyceride product into an isomerization unit 404 to yield a diesel fuel. One advantage of a separate unit to do isomerization is that it avoids hydrocracking of the fatty acid paraffins—which are already in the diesel boiling range.

Example 5

This Example serves to illustrate the integration of biofuels processing with GTL processing, wherein such integration occurs after the triglyceride product is hydrodeoxygenated.

Figure 5:
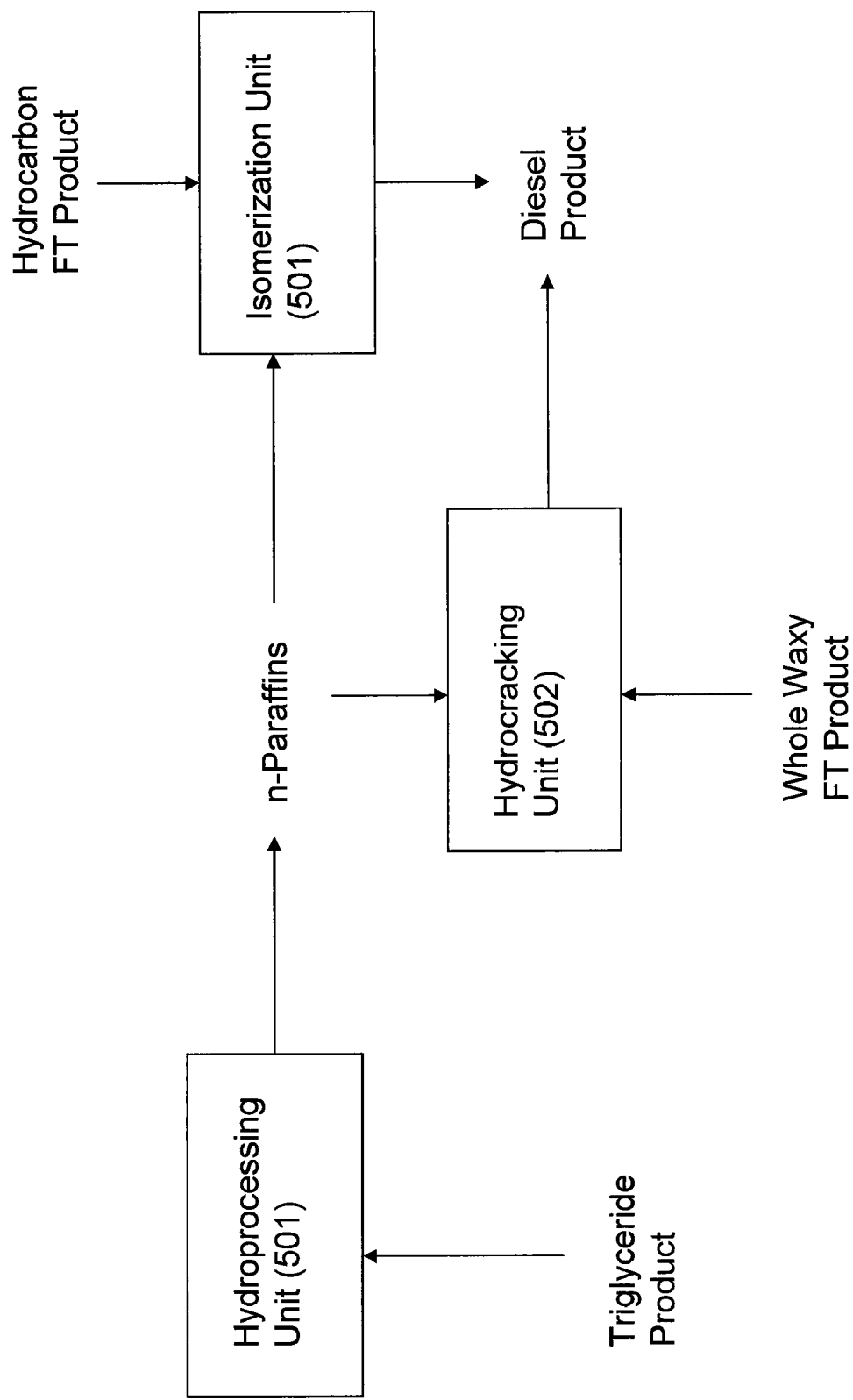
FIG. 5 illustrates, in flow diagram form, the integration of biofuels processing with GTL processing, wherein such integration occurs after the triglyceride product is hydrodeoxygenated.

Referring to FIG. 5, a triglyceride product is hydrodeoxygenated in hydroprocessing unit 501 to yield n-paraffins. These n-paraffins can then either be (a) co-fed with the whole waxy FT product (from the GTL processing) into hydrocracking unit 502; or they can be coifed with a hydrocracked FT product into isomerization unit 503. One advantage of hydrodeoxygenating the triglyceride product ahead of further hydroprocessing is that the product water can be separated out, since this water may affect downstream processing—including catalyst activity and stability.

7. Conclusion

In summary, the present invention is generally directed to systems and methods for integrating gas-to-liquids (GTL) processing with biofuels production, wherein $CO_2$ generated by GTL processing is used to support growth of microalgae from which triglycerides can be extracted and processed to yield transportation fuels. Thus, the present invention serves to mitigate many of the problems (described above) associated with $CO_2$ emissions and biofuels.

All patents and publications referenced herein are hereby incorporated by reference to the extent not inconsistent herewith. It will be understood that certain of the above-described structures, functions and operations of the above-described embodiments are not necessary to practice the present invention and are included in the description simply for completeness of an exemplary embodiment or embodiments. In addition it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

What is claimed:

1. A method comprising the steps of:
a) generating $CO_2$ in a gas-to-liquids plant;
b) using at least some of the $CO_2$ generated in the gas-to-liquids plant to grow microalgae by supporting photosynthesis in their growth cycle, wherein such growth yields harvestable microalgae;
c) harvesting the microalgae and processing the harvested microalgae to yield a triglyceride-based biofuel precursor comprising triglycerides;
d) hydroprocessing the triglyceride-based biofuel precursor to deoxygenate triglycerides contained therein and yield a paraffinic product; and
e) isomerizing the paraffinic product to yield a transportation fuel.

2. The method of claim 1, wherein at least one of the hydroprocessing and isomerizing steps are integrated with processes carried out in the gas-to-liquids plant.

3. The method of claim 2, wherein the triglyceride-based precursor is hydroprocessed together with gas-to-liquid-derived hydrocarbons.

4. The method of claim 2, wherein the paraffinic product is isomerized together with gas-to-liquid-derived paraffins.

5. The method of claim 1, wherein the gas-to-liquids plant is operable for producing transportation fuels.

6. The method of claim 5, wherein using at least some of the $CO_2$ generated in the gas-to-liquids plant to grow microalgae involves dissolving said $CO_2$ in an aqueous solution.

7. The method of claim 6, wherein the aqueous solution comprises saline water.

8. The method of claim 6, wherein the microalgae are contained within the aqueous solution.

9. The method of claim 6, wherein the aqueous solution is delivered to the microalgae.

10. The method of claim 5, wherein using at least some of the $CO_2$ generated in the gas-to-liquids plant to grow microalgae involves sequestering said $CO_2$ through the use of gas separation membranes and subsequently delivering the sequestered $CO_2$ to the microalgae.

11. The method of claim 5, wherein the step of harvesting comprises removal of at least some of the microalgae for subsequent processing.

12. The method of claim 11, wherein the subsequent processing serves to extract triglycerides from the microalgae.

13. The method of claim 11, wherein the subsequent processing comprises a process technique selected from the group consisting of dewatering, grinding, crushing, sonication, homogenization, solvent extraction, and combinations thereof.

14. The method of claim 5, wherein the triglyceride-based biofuel precursor comprises at least 75 weight percent triglycerides.

15. The method of claim 5, wherein the step of hydroprocessing comprising processing the triglyceride-based biofuel precursor in a hydrogen-containing environment in the presence of a catalyst.

16. The method of claim 5, wherein the paraffinic product comprises at least 75 weight percent paraffinic species.

17. The method of claim 16, wherein C5-C20 paraffins account for at least 75 weight percent of the paraffinic species.

18. The method of claim 5, wherein the step of isomerizing is carried using an isomerization catalyst.

19. The method of claim 5, further comprising a step of blending the transportation fuel with other transportation fuels.

20. The method of claim 5, wherein the transportation fuel is a low pour-point diesel.

21. The method of claim 1, wherein triglycerides obtained from sources other than microalgae are mixed with the triglyceride-based biofuel precursor prior to the latter being hydroprocessed.

22. The method of claim 21, wherein the triglycerides obtained from sources other than microalgae are derived from at least one source selected from the group consisting of vegetable oils and animal fats.

23. A system comprising:
a) a conventional gas-to-liquids plant that produces a $CO_2$ by-product;
b) a repeatedly-harvestable population of microalgae;
c) a means for directing the $CO_2$ to the microalgae to support growth thereof;
d) a means for harvesting the microalgae and extracting from it a triglyceride-based product comprising triglycerides;
e) a means for hydroprocessing at least a portion of the triglyceride-based product to deoxygenate triglycerides contained therein and yield a paraffin-based product; and f) a means for isomerizing at least a portion of the paraffin-based product to yield a transportation fuel.

24. The system of claim 23, wherein at least one of the means for hydroprocessing and the means for isomerizing are integral with the gas-to-liquids plant.

25. The system of claim 23, wherein the conventional gas-to-liquids plant is operable for producing transportation fuels.

26. The system of claim 23, wherein the means for directing the $CO_2$ to the microalgae comprises a subsystem means for sequestering the $CO_2$ produced in the gas-to-liquids plant.

27. The system of claim 26, wherein the subsystem means for sequestering the $CO_2$ produced in the gas-to-liquids plant involves filtration.

28. The system of claim 26, wherein the $CO_2$ is sequestered in an aqueous solution.

29. The system of claim 28, wherein the aqueous solution comprises the repeatedly-harvestable population of microalgae.

30. The system of claim 28, wherein the aqueous solution is delivered to the repeatedly-harvestable population of microalgae.

31. The system of claim 26, wherein the means for harvesting involves removal of at least some of the repeatedly-harvestable population of microalgae for subsequent processing.

32. The system of claim 31, wherein the extracting comprises a subsystem means selected from the group consisting of dewatering, grinding, crushing, sonication, homogenization, solvent extraction, and combinations thereof.

33. The system of claim 26, wherein the means for hydroprocessing comprises a catalyst and a hydrogen-containing environment.

34. The system of claim 26, wherein the means for isomerizing comprises an isomerization catalyst.

35. The system of claim 26, further comprising a means for blending the transportation fuel with other species to impart to it desirable properties.

* * * * *